United States Patent [19]

Massoud

[11] Patent Number: 5,776,097
[45] Date of Patent: Jul. 7, 1998

[54] METHOD AND DEVICE FOR TREATING INTRACRANIAL VASCULAR ANEURYSMS

[75] Inventor: Tarik F. Massoud, Los Angeles, Calif.

[73] Assignee: University of California at Los Angeles, Los Angeles, Calif.

[21] Appl. No.: 770,694

[22] Filed: Dec. 19, 1996

[51] Int. Cl.⁶ ............................................. A61M 31/00
[52] U.S. Cl. ........................ 604/49; 604/96; 604/101; 606/192
[58] Field of Search ...................... 604/49, 51–53, 604/96, 101–104; 606/191, 192

[56] References Cited

U.S. PATENT DOCUMENTS

| | | | |
|---|---|---|---|
| 5,195,971 | 3/1993 | Sirhan | 604/96 |
| 5,295,962 | 3/1994 | Crocker et al. | 604/101 |
| 5,409,459 | 4/1995 | Gambale | 604/96 |
| 5,536,250 | 7/1996 | Klein et al. | 604/102 X |
| 5,558,642 | 9/1996 | Schweich, Jr. et al. | 604/96 |
| 5,611,775 | 3/1997 | Machold et al. | 604/53 |

OTHER PUBLICATIONS

"Aneurysmal rebleeding: A preliminary report from the Cooperative Aneurysm Study." *Neurosurgery*, 1983, 13:479–481.

Wiebers DO, Torner JC, Meissner, I, "Impact of unruptured intracranial aneurysms on public health in the United States," *Stroke*, 1992, 23:1416–1419.

*Primary Examiner*—John D. Yasko
*Attorney, Agent, or Firm*—David A. Farah, M.D.; Sheldon & Mak

[57] ABSTRACT

A device and method for the therapeutic management of intracranial vascular aneurysms are provided involving the use of intravascular balloon catheters that can directly image the aneurysm and that can occlude the entire lumen of the aneurysm sac using liquid sealing agents. The intracranial catheters, according to the present invention, have various configurations designed to treat aneurysms regardless of the aneurysm's neck size and at different locations within the intracranial vascular system.

12 Claims, 6 Drawing Sheets

METHOD AND DEVICE FOR TREATING INTRACRANIAL VASCULAR ANEURYSMS

BACKGROUND

Stroke refers to a disease of vascular origin characterized by a neurologic deficit of acute or subacute onset. Stroke is the most common life-threatening neurologic disease and is the third leading cause of death in developed countries after heart disease and cancer.

Approximately 6 to 8 percent of all strokes result from nontraumatic subarachnoid hemorrhage (SAH), a condition where blood leaks from the cerebral vasculature into the subarachnoid space. Approximately eighty percent of subarachnoid hemorrhages results from rupture of an intracranial aneurysm. See, for example, "Aneurysmal rebleeding: A preliminary report from the Cooperative Aneurysm Study," *Neurosurgery*, 1983, 13:479–481, incorporated herein by reference in its entirety.

An aneurysm is an abnormal, circumscribed dilation of a blood vessel. In the cerebral circulation, most aneurysms take the form of thin-walled sacs protruding from the arteries of the circle of Willis at the base of the brain, or from its branches.

Autopsy studies estimate that the prevalence of intracranial aneurysms larger than about 4 mm is approximately 5 percent. If aneurysms as small as 2 mm are considered, however, 17 percent of routine autopsies reveal at least one unruptured intracranial aneurysm.

Generally, intracranial aneurysms are diagnosed in vivo only after they rupture. In the United States, the peak age at which intracranial aneurysms rupture is between the fifth and the seventh decades. Clinically, the frequency of ruptured intracranial aneurysms has been estimated at approximately 11 per 100,000 population per year. Although the total incidence stroke appears to be declining, the incidence of stroke from SAH is remaining stable.

Ruptured intracranial aneurysms are associated with a high rate of mortality. Approximately fifteen percent of patients die soon after the initial rupture. An additional 20 to 30 percent of patients die during the first two weeks following the initial rupture.

Rebleeding is one of the major causes of death in the patients who survive the initial hemorrhage. The mortality rate associated with the second hemorrhage is between 40 and 50 percent. If untreated, the risk of rebleeding is about 20 percent during the first two weeks after the initial hemorrhage, about 33 percent at one month after the initial hemorrhage, and about 50 percent at six months after the initial hemorrhage. The risk of rebleeding in untreated patients gradually diminishes to approximately 3 percent annually.

In addition to the high mortality rate associated with ruptured intracranial aneurysms, there is also a high morbidity rate among patients who survive the rupture long term. Almost two-thirds of patients well enough to be discharged home after surgical obliteration of the aneurysm have a residual neurological deficit.

The estimated lifetime cost of hospitalization and treatment of patients for annual cases of patients hospitalized with unruptured intracranial aneurysms is estimated to exceed $500,000,000 in the United States and for patients with SAH due to ruptured intracranial aneurysms is estimated to exceed $1,750,000,000. See, for example, Wiebers D O, Tomer J C, Meissner I. "Impact of unruptured intracranial aneurysms on public health in the United States," *Stroke*, 1992, 23:1416–1419. Therefore, both ruptured and unruptured intracranial aneurysms constitute a significant public health problem.

The optimum treatment of intracranial aneurysms would be to totally occlude the aneurysm while preserving the parent artery, with minimal procedure morbidity and mortality. In recent decades, the main surgical treatment of ruptured and unruptured intracranial aneurysms has been to expose the aneurysm in an open cranial procedure and to ligate the neck of the aneurysm using surgical clips. These open surgical procedures carry a significant degree of morbidity and mortality. Further, some intracranial aneurysms are located deep within the intracranial cavity and are not easily amenable to exposure by open procedures.

During the last two decades, endovascular treatment in selected cases of brain aneurysms has emerged as a therapeutic alternative to open surgery. Currently, the most commonly used method for endovascular occlusion of intracranial aneurysms involves the use of the Guglielmi Detachable Coil (GDC) electrolytically detachable coils (manufactured by Target Therapeutics, Fremont, Calif.). While this method represents an advance in the treatment of intracranial aneurysms, the method has several disadvantages. For example, the method involves the placement of a solid foreign body within the aneurysm sac which can cause the aneurysm to rupture. Secondly, the method tends to leave aneurysm remnants, particularly when used to treat aneurysms having a wide-necked configuration.

There remains, therefore, a need for a device and method for therapeutically treating intracranial aneurysms that does not require an open procedure. Further, there remains a need for a device and method for therapeutically treating intracranial aneurysms that allow for occlusion of the entire aneurysm sac regardless of its configuration. Further, there remains a need for a device and method for therapeutically treating intracranial aneurysms soon after the initial rupture that is associated with low morbidity and mortality.

SUMMARY

According to one embodiment of the present invention, there is provided a device for treating an intracranial vascular aneurysm located on an intracranial blood vessel. The device comprises a catheter having a first inflation balloon, means for visualizing the blood vessel lumen adjacent the aneurysm lumen, and means for delivering a liquid sealing agent to the aneurysm lumen. In a preferred embodiment, the device further includes at least one additional inflation balloon.

According to another embodiment of the present invention, there is provided a method of treating an aneurysm of an intracranial blood vessel. The method includes the steps of, first, inserting a catheter having a proximal end and a distal end into the blood vessel containing the aneurysm. The catheter includes a central lumen and an inflation conduit connected to an inflation balloon. Next, the catheter is advanced until the distal end is proximate the aneurysm. Then, the inflation balloon is inflated such that the balloon and catheter substantially occlude the blood vessel adjacent the aneurysm. Next, a sealing agent is delivered through the central lumen into the aneurysm sufficient to substantially fill the aneurysm. The method can further include the step of delivering an irrigation substance into the blood vessel adjacent the aneurysm through the central lumen to substantially remove blood from aneurysm sac and blood vessel adjacent the aneurysm, thereby creating a substantially clear view of the aneurysm sac. The method can also include the

3 step of inflating one or more additional balloon to block backflow from the blood vessel or from collateral blood vessels.

FIGURES

These and other features, aspects and advantages of the present invention will become better understood with regard to the following description, appended claims, and accompanying figures where:

4

DESCRIPTION

According to one embodiment of the present invention, there is provided a device and method for the therapeutic management of intracranial vascular aneurysms. The invention involves the use of intravascular balloon catheters that can directly image the aneurysm and that can occlude the lumen of the aneurysm sac using liquid sealing agents. The intracranial catheters, according to the present invention, have various configurations designed to treat aneurysms at different locations within the intracranial vascular system.

Figure 1:
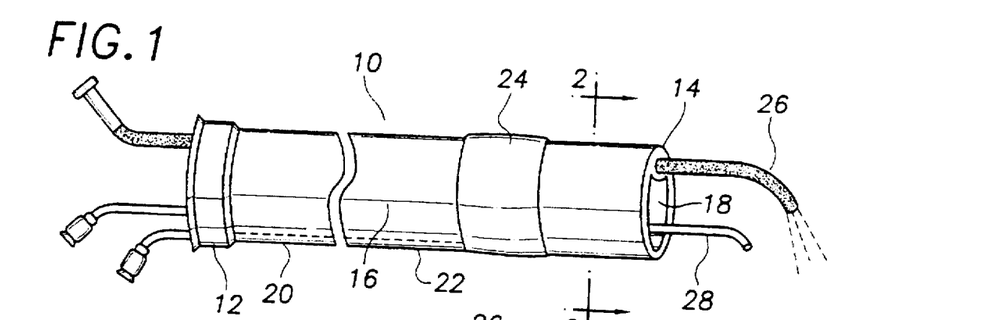
FIG. 1 is a fragmentary side elevational view of an intravascular catheter according to one embodiment of the present invention.
Figure 2:
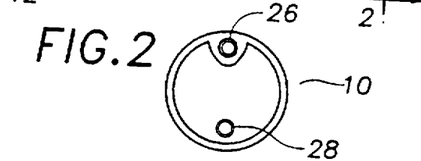
FIG. 2 is a cross-sectional view of the intravascular catheter shown in FIG. 1 taken along the line 2—2.

Referring now to FIGS. 1 and 2, there is shown, respectively, a fragmentary side elevational view of an intravascular catheter according to one embodiment of the present invention and a cross-sectional view of the intravascular catheter shown in FIG. 1 taken along the line 2—2. The catheter 10 is particularly useful to occlude intracranial aneurysms located such that, upon occlusion of the blood vessel proximal to the aneurysm by the inflated inflation balloon, there is minimal backflow of blood into the aneurysm from the parent artery or from adjacent collateral blood vessels.

The catheter 10 comprises a proximal end 12, a distal end 14, a body 16 between the proximal end 12 and the distal end 14, and a central lumen 18 extending through the catheter from the proximal end 12 to the distal end 14. As used herein, "central lumen" refers to one or more coaxial lumens within the body 16 of the catheter 10.

The catheter further comprises a first inflation conduit 20 having a distal end 22, and a first inflation balloon 24 in communication with the distal end 22 of the inflation conduit 20. The first inflation balloon 24 can be made of latex or other biocompatible material as will be understood by those with skill in the art with reference to the disclosure herein. In a preferred embodiment, the first inflation balloon 24 comprises silicon because this material can be inflated sufficiently to occlude a blood vessel while placing less tension on the wall of the blood vessel than with an equivalent latex inflation balloon.

The first inflation balloon 24 can be configured to adjoin only part of the circumference of the body 16 of the catheter 10 when inflated. In a preferred embodiment, as shown in FIGS. 1 and 2, the first inflation balloon 24 is configured to substantially surround the body 16 of the catheter 10 when inflated. In another preferred embodiment, the inflation balloon 24 is configured to occlude blood vessel having diameters between about 2 mm and about 6 mm when inflated. In yet another preferred embodiment, the first inflation balloon 24 ends between about 5 mm and about 10 mm from the distal end 12 of the catheter 10.

The outer diameter of the catheter 10 should be as small as possible to allow access to aneurysms in more distal portions of the intracranial vascular system. In a preferred embodiment, the outer diameter of the catheter is less than about 1.5 mm, that is less than about 5 F. In another preferred embodiment, the outer diameter of the catheter should be between about 0.6 mm and 1.2 mm, that is between about 2 F and 4 F. Further, the catheter should be as flexible enough to allow access to aneurysms in more distal portions of the intracranial vascular system.

The catheter 10 further includes, in combination with the central lumen, means for visualizing the blood vessel lumen adjacent to the aneurysm lumen. The means for visualizing can include a microangioscope 26. The microangioscope 26 can have a straight tip or a curved tip depending on the configuration of the aneurysm to be treated, as will be understood by those with skill in the art with reference to the disclosure herein. To keep the catheter diameter as small as possible and for other reasons, it is advantageous to use the smallest diameter microangioscope 26 which is suitable for visualizing the internal anatomy of the blood vessel and aneurysm. In a preferred embodiment, the microangioscope 26 has a diameter of less than approximately 0.25 mm. Suitable microangioscopes are available, for example, from Mitsuhishi Cable America, Inc., Davis, Calif., USA.

The catheter 10 further includes, in combination with the central lumen 18, means for delivering a liquid sealing agent. The means for delivering a liquid sealing agent can include a microcatheter 28. Preferably, the microcatheter 28 is pre-shaped to assist in delivering the liquid sealing agent directly into the lumen of the aneurysm sac as will be understood by those with skill in the art with reference to the disclosure herein. Further, the microcatheter 28 should have as small a diameter as possible suitable for its function. In a preferred embodiment, the microcatheter 28 will have an outer diameter of less than approximately 0.3 mm, that is about 1 F. Suitable microcatheters are available, for example, from Target Therapeutics, Fremont, Calif., USA.

Figure 3:
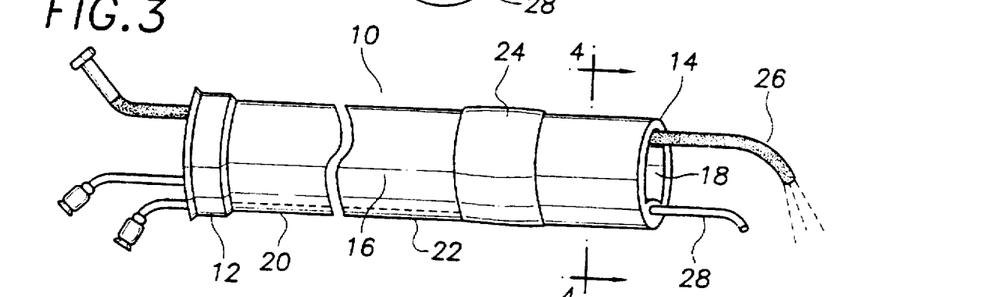
FIG. 3 is a fragmentary side elevational view of an intravascular catheter according to another embodiment of the present invention.
Figure 4:
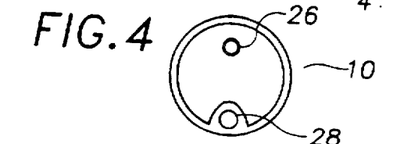
FIG. 4 is a cross-sectional view of the intravascular catheter shown in FIG. 3 taken along the line 4—4.
Figure 5:
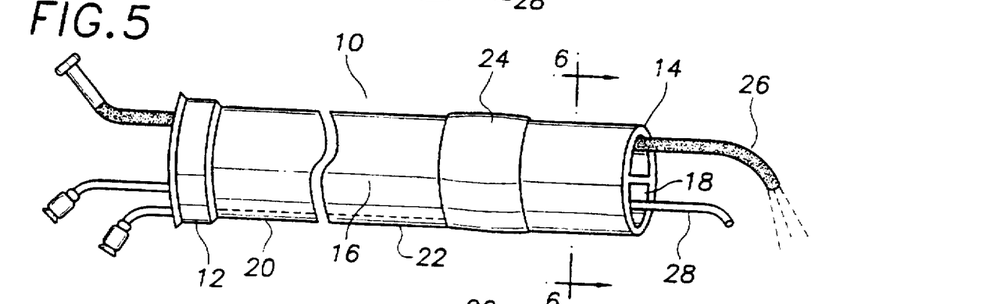
FIG. 5 is a fragmentary side elevational view of an intravascular catheter according to another embodiment of the present invention.
Figure 6:
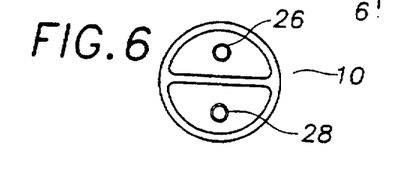
FIG. 6 is a cross-sectional view of the intravascular catheter shown in FIG. 5 taken along the line 6—6.

Referring now to FIGS. 3 through 6, there are shown respectively a fragmentary side elevational view of an intravascular catheter according to an embodiment of the present invention, a cross-sectional view of the intravascular catheter shown in FIG. 3 taken along the line 4—4, a fragmentary side elevational view of an intravascular catheter according to another embodiment of the present invention, and a cross-sectional view of the intravascular catheter shown in FIG. 5 taken along the line 6—6. The two embodiments of the catheter 10 shown in FIGS. 3 through 6 have similar features to the embodiment shown in FIGS. 1 and 2 as indicated by the numbered elements. The embodiments shown in FIGS. 1 through 6 differ in the relation of the microangioscope 26 and microcatheter 28 to the wall of the catheter body 16. As can be seen, in the embodiment shown in FIGS. 1 and 2, the microangioscope 26 is fixed within the wall of the catheter body 16 and the microcatheter 28 is not fixed within the wall of the catheter body 16. By comparison, in the embodiment shown in FIGS. 3 and 4, the microangioscope 26 is not fixed within the wall of the catheter body 16 while the microcatheter 28 is fixed within the wall of the catheter body 16. Further, in the embodiment shown in FIGS. 5 and 6, neither the microangioscope 26 nor the microcatheter 28 is fixed within the wall of the catheter body 16. The particular embodiment most appropriate for occluding an intracranial aneurysm depends upon whether the adjacent anatomy would be most easily accessed by having the microangioscope 26 or the microcatheter 28 movable relative to the catheter body 16 as will be understood by those with skill in the art with reference to the disclosure herein.

Figures 7, 8, 9:
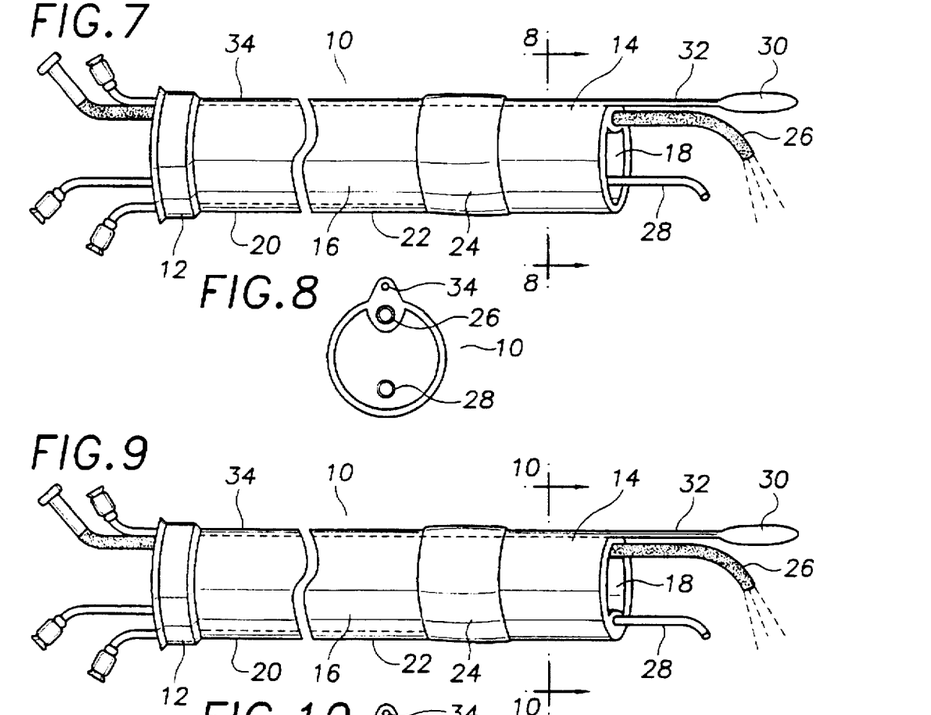
FIG. 7 is a fragmentary side elevational view of an intravascular catheter according to one embodiment of the present invention.
FIG. 8 is a cross-sectional view of the intravascular catheter shown in FIG. 7 taken along the line 8—8.
FIG. 9 is a fragmentary side elevational view of an intravascular catheter according to another embodiment of the present invention.
Figures 10, 11:
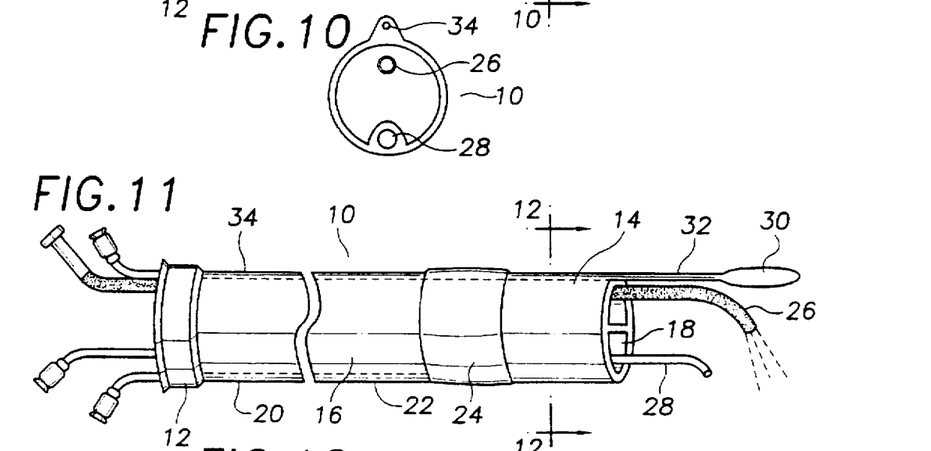
FIG. 10 is a cross-sectional view of the intravascular catheter shown in FIG. 9 taken along the line 10—10.
FIG. 11 is a fragmentary side elevational view of an intravascular catheter according to another embodiment of the present invention.
Figure 12:
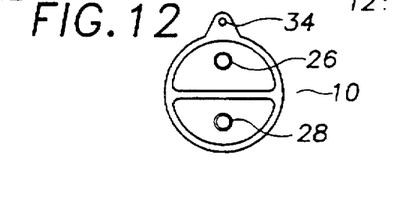
FIG. 12 is a cross-sectional view of the intravascular catheter shown in FIG. 11 taken along the line 12—12.

Referring now to FIGS. 7 through 12, there are shown respectively a fragmentary side elevational view of an intravascular catheter according to one embodiment of the present invention, a cross-sectional view of the intravascular catheter shown in FIG. 7 taken along the line 8—8, a fragmentary side elevational view of an intravascular catheter according to another embodiment of the present invention, is a cross-sectional view of the intravascular catheter shown in FIG. 9 taken along the line 10—10, a fragmentary side elevational view of an intravascular catheter according to another embodiment of the present invention, and a cross-sectional view of the intravascular catheter shown in FIG. 11 taken along the line 12—12. As can be seen, each embodiment depicted in FIGS. 7 through 12 corresponds to an embodiment shown in FIGS. 1 through 6 respectively, except that each embodiment shown in FIGS. 7 through 12 includes a second inflation balloon 30 in addition to the first inflation balloon 24. The second inflation balloon 30 is in communication with the distal end 32 of a second inflation conduit 34. The second inflation conduit 34 can be an extension of the first inflation conduit 20, or can be an entirely separate conduit, as shown. Further, the second inflation conduit 34 can be fixed within the wall of the catheter 16 or movable within the wall of the catheter 16. If the second inflation conduit 34 and second inflation balloon 30 are moveable within the wall of the catheter 16, it is preferred that the second inflation conduit 34 and second inflation balloon 30 are preassembled into the catheter 16 prior to use.

The catheter 10 shown in FIGS. 7 through 12 is particularly useful for treating intracranial aneurysms located such that, upon occlusion of the blood vessel proximal to the aneurysm, there is significant backflow of blood into the aneurysm from one additional source other than from the parent blood vessel proximally. The second inflation balloon 30 is inflated distally to the aneurysm to occlude the parent artery having the aneurysm when, for example, there is significant backflow of blood into the aneurysm even though the parent artery is occluded proximally to the aneurysm. Before trapping the aneurysm between the first inflation balloon 24 and the second inflation balloon 30, any trapped blood between the first inflation balloon 24 and the second inflation balloon 30 is replaced with a substance such as clear fluid, for example 5% dextrose solution, or carbon dioxide to allow angioscopic monitoring of the treatment. Further, small amounts of flow from collateral vascular branches can be controlled with low volume continuous irrigation via the lumen of the microangioscope 26 in order to maintain a clear angioscopic field. This embodiment advantageously allows trapping of the aneurysm without the necessity of using two single balloon catheters simultaneously in the same artery.

Figures 13, 14:
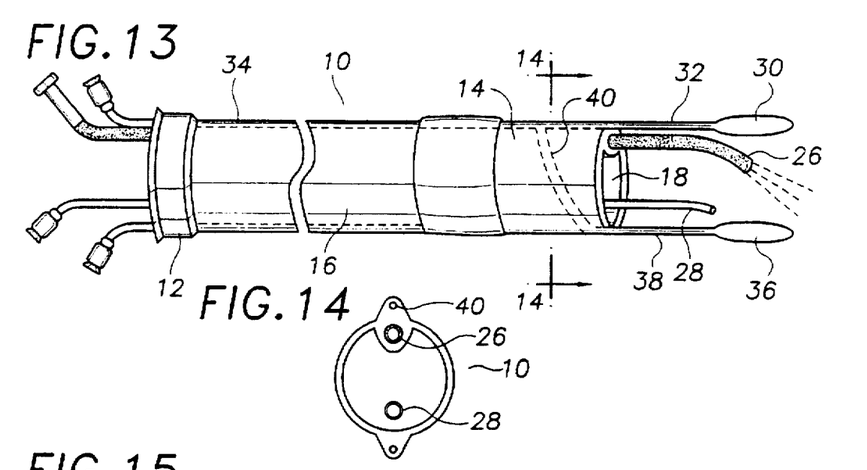
FIG. 13 is a fragmentary side elevational view of an intravascular catheter according to one embodiment of the present invention.
FIG. 14 is a cross-sectional view of the intravascular catheter shown in FIG. 13 taken along the line 14—14.
Figures 15, 16:
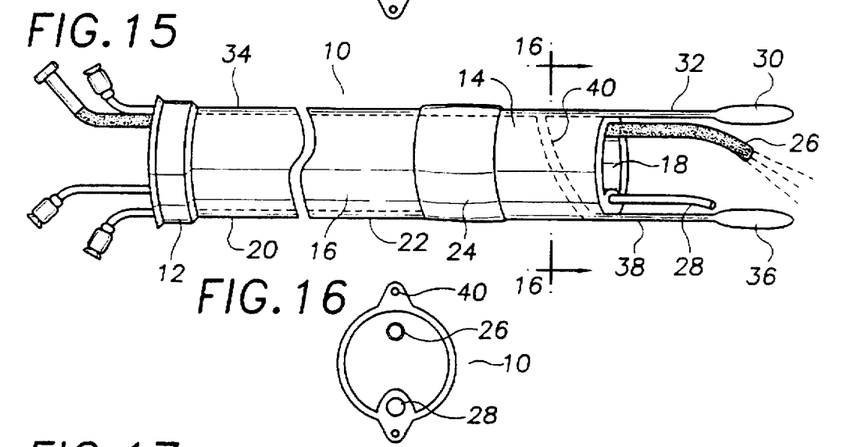
FIG. 15 is a fragmentary side elevational view of an intravascular catheter according to another embodiment of the present invention.
FIG. 16 is a cross-sectional view of the intravascular catheter shown in FIG. 15 taken along the line 15—15.
Figures 17, 18:
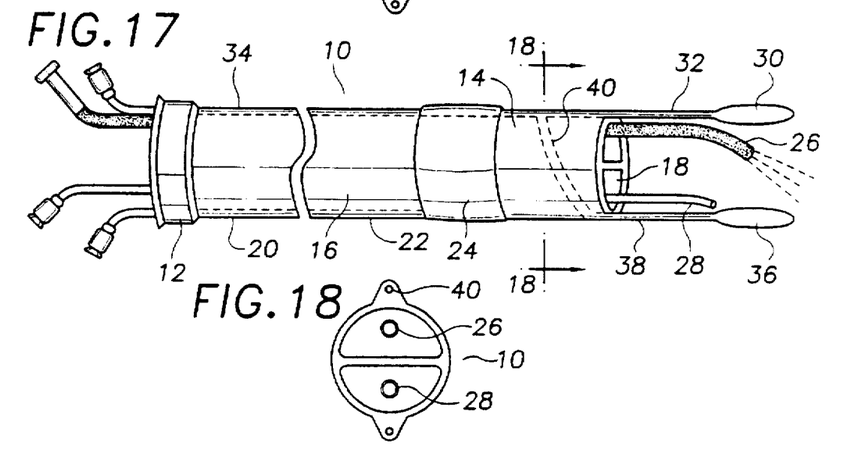
FIG. 17 is a fragmentary side elevational view of an intravascular catheter according to another embodiment of the present invention.
FIG. 18 is a cross-sectional view of the intravascular catheter shown in FIG. 17 taken along the line 18—18.

Referring now to FIGS. 13 through 18, there are shown respectively a fragmentary side elevational view of an intravascular catheter according to one embodiment of the present invention, a cross-sectional view of the intravascular catheter shown in FIG. 13 taken along the line 14—14, a fragmentary side elevational view of an intravascular catheter according to another embodiment of the present invention, is a cross-sectional view of the intravascular catheter shown in FIG. 15 taken along the line 16—16, a fragmentary side elevational view of an intravascular catheter according to another embodiment of the present invention, and a cross-sectional view of the intravascular catheter shown in FIG. 17 taken along the line 18—18. As can be seen, each embodiment depicted in FIGS. 13 through 18 corresponds to an embodiment shown in FIGS. 7 through 12 respectively, except that each embodiment shown in FIGS. 13 through 18 includes a third inflation balloon 36 in addition to the first inflation balloon 24 and a second inflation balloon 30. The third inflation balloon 36 is in communication with the distal end 38 of a third inflation conduit 40. The third inflation conduit 40 can be an extension of the first inflation conduit 20, or can be an entirely separate conduit, as shown. Further, the third inflation conduit 40 can be fixed within the wall of the catheter 16 or movable within the wall of the catheter 16. If the third inflation conduit 40 and third inflation balloon 36 are moveable within the wall of the catheter 16, it is preferred that the third inflation conduit 40 and third inflation balloon 36 are preassembled into the catheter 16 prior to use.

The catheter 10 shown in FIGS. 13–18 is particularly useful for treating intracranial aneurysms located such that, upon occlusion of the blood vessel proximal to the aneurysm, there is significant backflow of blood into the aneurysm from two additional vascular sources other than from the parent blood vessel proximally. The second inflation balloon 30 and the third inflation balloon 36 are inflated to occlude blood vessels that cause significant backflow of blood into the aneurysm even though the parent artery is occluded proximally to the aneurysm. Before trapping the aneurysm between the first inflation balloon 24, the second inflation balloon 30 and the third inflation balloon 36, any trapped blood is replaced with a substance such as clear fluid, for example 5% dextrose solution, or carbon dioxide to allow angioscopic monitoring the treatment. Further, small amounts of flow from collateral vascular branches can be controlled with low volume continuous irrigation via the microangioscope lumen in order to keep a clear angioscopic field. This embodiment advantageously allows trapping of the aneurysm without the necessity of using multiple single balloon catheters simultaneously in the same blood vessel.

According to another embodiment of the present invention, there is provided a method for treating an aneurysm of an intracranial blood vessel using a liquid sealing agent to seal the lumen of the aneurysm. The method comprises providing a catheter configured to preform the method as disclosed herein. In a preferred embodiment, the catheter provided is an embodiment of the device disclosed herein.

Using techniques as will be understood by those with skill in the art with reference to the disclosure herein, the catheter is passed into the vasculature of a patient having an intracranial aneurysm and advanced into the patient's cerebral circulation. Insertion of the catheter can be performed, for example, using a conventional microguidewire. Alternately, the catheter is advanced using steerable technology. Use of steerable technology advantageously reduces the overall size of the catheter allowing for access to aneurysms located more distally in the cerebral circulation. Alternately, or in combination, steerable technology can be used in conjunction with the component parts of the catheter. The distal end of the catheter is advanced into the cerebral circulation to a point just proximal of the aneurysm.

Next, the microguidewire, if used, is removed and a microangioscope inserted in the microguidewire lumen. Otherwise, a microangioscope is inserted into an appropriately sized lumen within the catheter body. Then, an inflation balloon attached at or near the distal end of the catheter is inflated. The inflated inflation balloon creates a seal between the catheter and the lumen of the blood vessel proximal to the aneurysm. Preferably, the inflated inflation balloon surrounds the circumference of the catheter body. The balloon may be inflated with a radiographically visible gas such as carbon dioxide to permit visualization on digital subtraction images, thereby reducing the overall outer diameter of the catheter.

Next, clear fluid irrigation is started using the lumen for the microangioscope, using a separate lumen or using both the lumen for the microangioscope and a separate lumen. The lumen or lumens used for irrigation depends on the volume of irrigation necessary for the particular location within the cerebral circulation. In order to use the microangioscope lumen for irrigation, as well as to keep the catheter diameter as small as possible and for other reasons, it is advantageous to use the smallest diameter microangioscope which is suitable for visualizing the internal anatomy of the blood vessel and aneurysm.

Once a clear angioscopic field is established, if not before, the patient is positioned to render the lumen of the aneurysm sac gravity dependent. This can be performed or confirmed using techniques such as radiographic positioning. Then, a microcatheter is placed through a microcatheter lumen in the catheter such that the distal tip of the microcatheter opens into the aneurysm sac. The microcatheter lumen is, preferably, adjacent and coaxial with the lumen for the microangioscope. It is preferred that the microcatheter lumen is separate from the microangioscope lumen so that passage and maneuverability of both the microangioscope and microcatheter carrying the sealing agent is smooth and without interference from each other. Satisfactory microcatheter positioning is confirmed by angioscopy, fluoroscopy or other appropriate techniques.

After satisfactory placement of the microcatheter, endovascular placement of a liquid sealing agent within the aneurysm is begun utilizing the gravity dependent position of the aneurysm sac. Placement of the liquid sealing agent is accomplished by passing the liquid sealing agent through the microcatheter and into the lumen of the aneurysm sac. Advantageously, pressure does not build up in the sac of the aneurysm because of decompression through the proximal end of the catheter via the microangioscope lumen or the microcatheter lumen. Suitable liquid sealing agents are biocompatible, set relatively fast and are amenable to passage through microcatheters. Further, suitable liquid sealing agents are preferably either radiopaque or can be rendered radiopaque by the addition of a contrast agent or metal powder. An example of a suitable sealing agent is N-butyl cyanoacrylate (such as Histoacryl Blue®, available from Braun, Melsungen, Germany). The liquid sealing agent is slowly dripped into the aneurysm sac and allowed to set or polymerize. The level of the liquid sealing agent in the aneurysm sac is monitored directly by angioscopy and can be confirmed by external X-ray fluoroscopy when using a radiopaque sealing agent. Once satisfactory filling of the aneurysm sac is accomplished, the flow of liquid sealing agent is stopped.

If a clear angioscopic field cannot be established using the method described above because of backflow of blood from the parent artery or flow from collateral blood vessels, one or more additional steps can be incorporated into the method to create a clear angioscopic field. These steps include positioning one or more additional inflation balloons, connected to additional inflation conduits in the catheter wall, into the blood vessel having the aneurysm. The additional balloon or balloons are then inflated to occlude the blood vessels which are the source of the blood flow obstructing the field including the aneurysm sac, thereby trapping the aneurysm between the various inflation balloons.

Figures 19, 20, 21, 22:
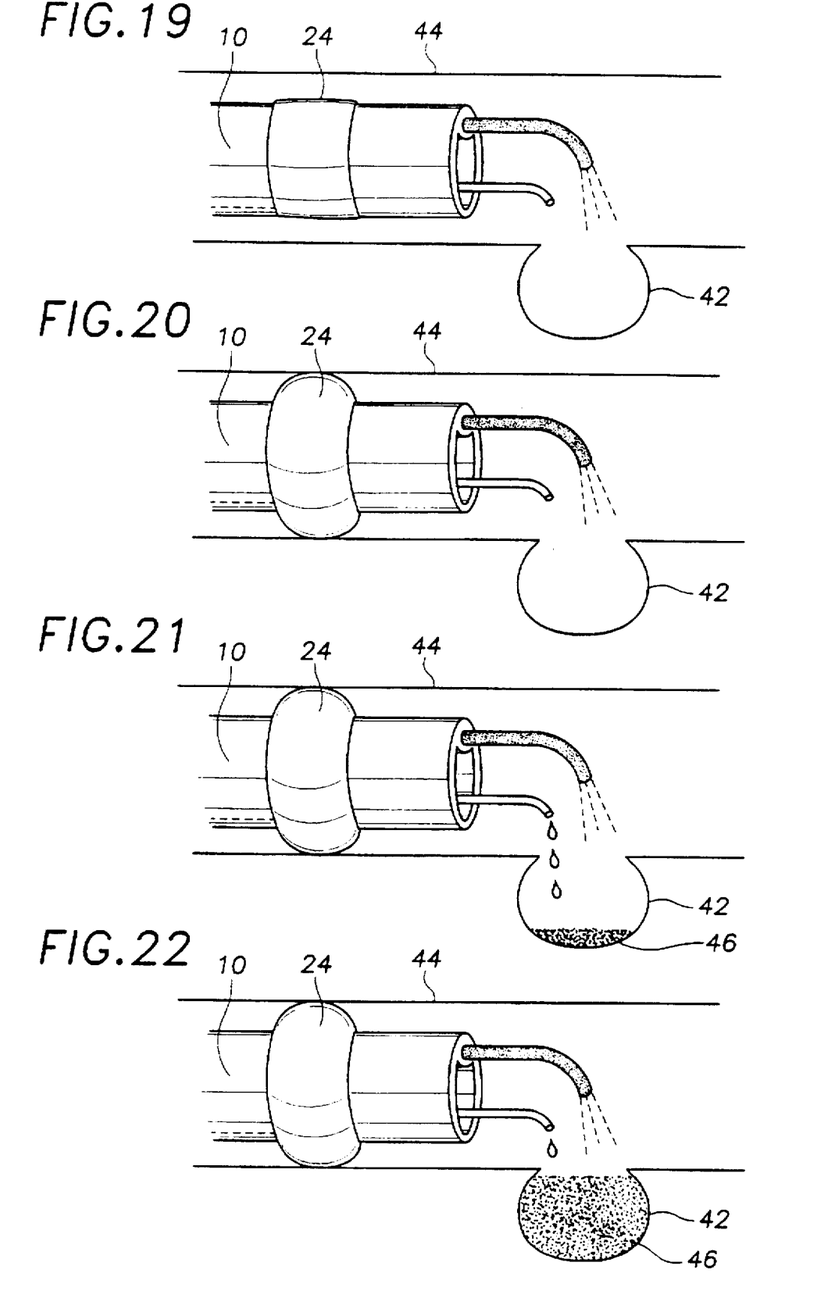
FIGS. 19–22 show partial views of the distal end of the catheter illustrated in FIGS. 1 and 2 being used to occlude the lumen of an intracranial aneurysm.

Referring now to FIGS. 19 through 22, there are shown partial views of the distal end of the catheter 10 illustrated in FIGS. 1 and 2 being used to occlude the lumen of an intracranial aneurysm 42 according to the method described above. FIG. 19 shows the position of the catheter 10 in an artery 44 having the aneurysm 42 prior to inflation of the first inflation balloon 24. FIG. 20 shows the catheter 10 after inflation of the first inflation balloon 24 and occlusion of the artery 44 containing the aneurysm 42. FIG. 21 shows initiation of placement of the liquid sealing agent 46 into the lumen of the aneurysm 42. Finally, FIG. 22 shows completion of placement of the liquid sealing agent 46 into the lumen of the aneurysm 42.

Figure 23:
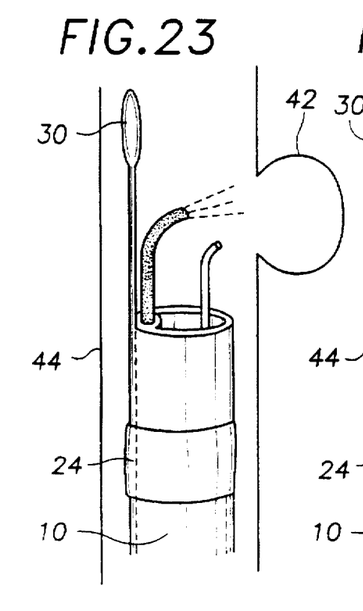
FIGS. 23–27 show partial views of the distal end of the catheter illustrated in FIGS. 7 and 8 being used to occlude the lumen of an intracranial aneurysm.
Figures 24, 25:
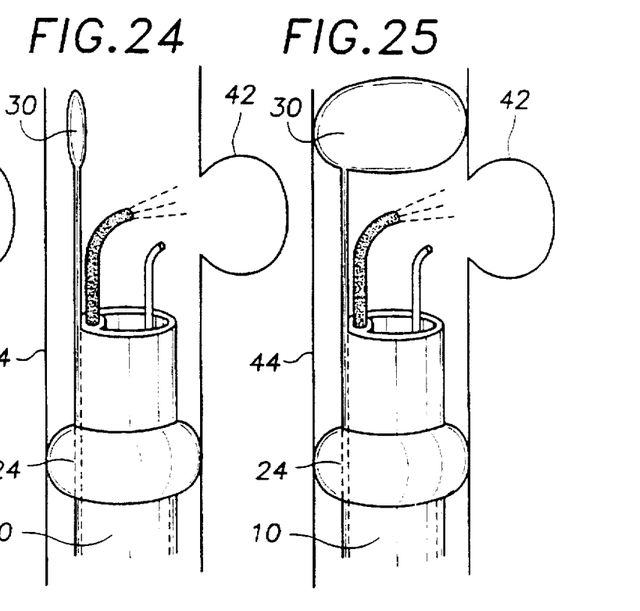
Figure 26:
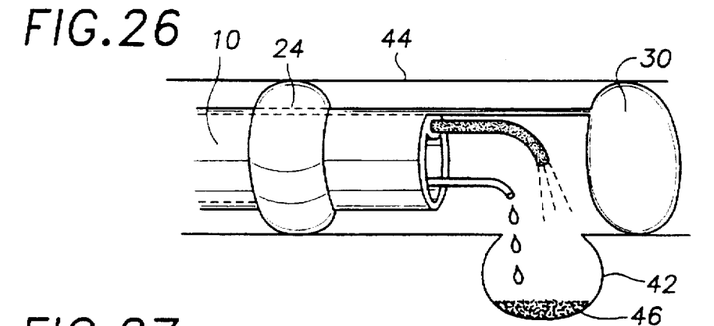
Figure 27:
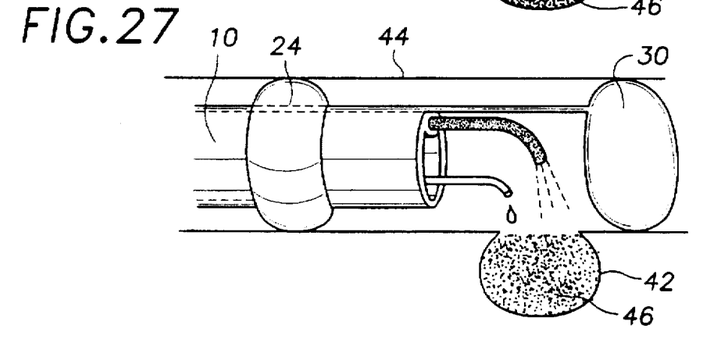

Referring now to FIGS. 23 through 27, there are shown partial views of the distal end of the catheter 10 illustrated in FIGS. 7 and 8 being used to occlude the lumen of an intracranial aneurysm 42. FIG. 23 shows the position of the catheter 10 in an artery 44 having the aneurysm 42 prior to inflation of the first inflation balloon 24. FIG. 24 shows the catheter 10 after inflation of the first inflation balloon 24. FIG. 25 shows the catheter 10 after inflation of the second inflation balloon 30 and occlusion of the artery 44 containing the aneurysm 42 both proximal and distal to the aneurysm. FIG. 26 shows initiation of placement of the liquid sealing agent 46 into the lumen of the aneurysm 42. Finally, FIG. 27 shows completion of placement of the liquid sealing agent 46 into the lumen of the aneurysm 42.

Figure 28:
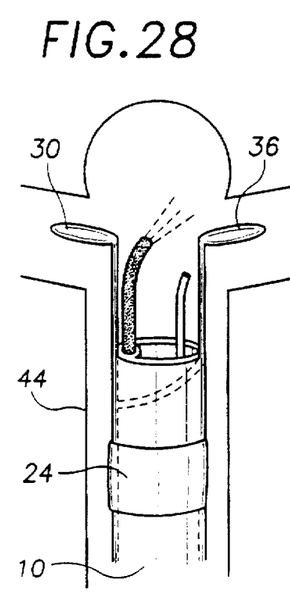
FIGS. 28–32 show partial views of the distal end of the catheter illustrated in FIGS. 13 and 14 being used to occlude the lumen of an intracranial aneurysm.
Figure 29:
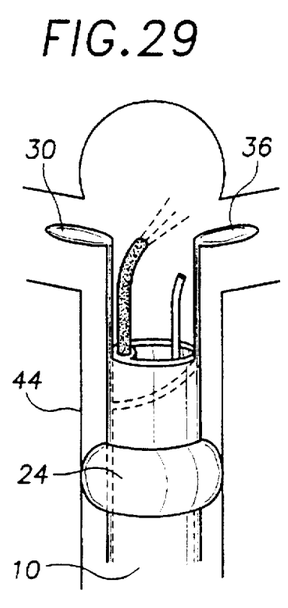
Figure 30:
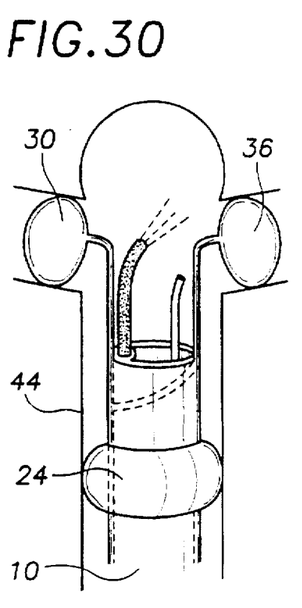
Figure 31:
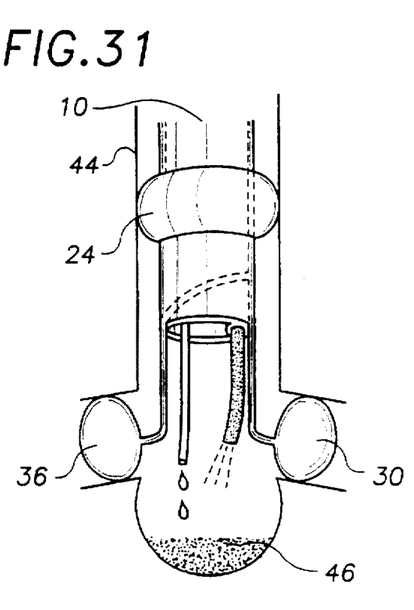
Figure 32:
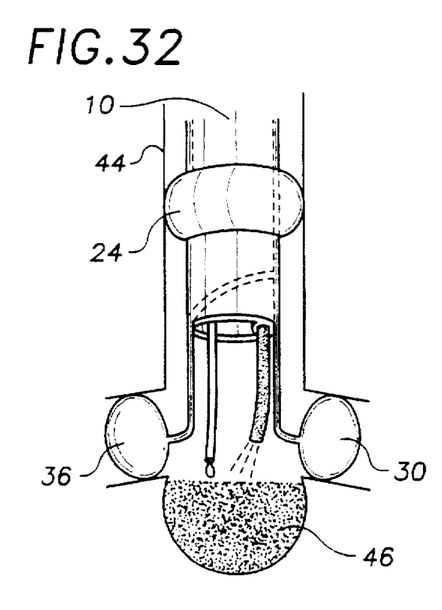

Referring now to FIGS. 28 through 32, there are shown partial views of the distal end of the catheter 10 illustrated in FIGS. 13 and 14 being used to occlude the lumen of an intracranial aneurysm 42. FIG. 28 shows the position of the catheter 10 in an artery 44 having the aneurysm 42 prior to inflation of the first inflation balloon 24. FIG. 29 shows the catheter 10 after inflation of the first inflation balloon 24. FIG. 30 shows the catheter 10 after inflation of the second inflation balloon 30 and the third inflation balloon 36, and occlusion of the artery 44 containing the aneurysm 42 both proximal and distal to the aneurysm. FIG. 31 shows initiation of placement of the liquid sealing agent 46 into the lumen of the aneurysm 42. Finally, FIG. 32 shows completion of placement of the liquid sealing agent 46 into the lumen of the aneurysm 42.

As will be understood by those with skill in the art with reference to the disclosure herein, corresponding methods of occluding intracranial aneurysms can be used for the other embodiments of the device disclosed herein.

Although the present invention has been discussed in considerable detail with reference to certain preferred embodiments, other embodiments are possible. Therefore, the spirit and scope of the appended claims should not be limited to the description of preferred embodiments contained herein.

I claim:

1. A device for treating an intracranial vascular aneurysm located on an intracranial blood vessel, the blood vessel having a lumen and the aneurysm having a lumen, the device comprising:

a catheter including a central lumen therethrough, a first inflation conduit having a distal end, and a first inflation balloon in communication with the distal end of the inflation conduit;

the catheter further including means for visualizing the blood vessel lumen adjacent the aneurysm lumen, the means for visualizing in combination with the central lumen; and the catheter further including means for delivering a liquid sealing agent to the lumen of the aneurysm, the means for delivering in combination with the central lumen.

2. The device of claim 1, wherein the first inflation balloon is configured to substantially surrounds the central lumen when the first inflation balloon is inflated.

3. The device of claim 1, wherein the means for visualizing comprises a microangioscope.

4. The device of claim 1, wherein the means for delivering comprises a microcatheter.

5. The device of claim 1, further including a second inflation conduit having a distal end, and a second inflation balloon in communication with the distal end of the second inflation conduit.

6. The device of claim 5, further including a third inflation conduit having a distal end, and a third inflation balloon in communication with the distal end of the third inflation conduit.

7. A device for treating an intracranial vascular aneurysm located on an intracranial blood vessel, the blood vessel having a lumen and the aneurysm having a lumen, the device comprising:

a catheter including a central lumen therethrough, an inflation conduit having a distal end, and an inflation balloon in communication with the distal end of the inflation conduit;

the catheter further including means for visualizing the blood vessel lumen adjacent the aneurysm lumen, the means for visualizing in combination with the central lumen;

the catheter further including means for delivering a liquid sealing agent to the aneurysm lumen, the means for delivering in combination with the central lumen;

the catheter further including in combination with the central lumen, a second inflation conduit having a distal end, and a second inflation balloon in communication with the distal end of the second inflation conduit; and the catheter further including in combination with the central lumen, a third inflation conduit having a distal end, and a third inflation balloon in communication with the distal end of the third inflation conduit.

8. A method of treating an aneurysm of an intracranial blood vessel, the aneurysm having a sac, the method comprising the steps of:

(a) inserting a catheter having a proximal end and a distal end into the blood vessel containing the aneurysm, wherein the catheter includes a central lumen therethrough, and wherein the catheter further includes an inflation conduit connected to an inflation balloon;

(b) advancing the catheter until the distal end is proximate the aneurysm;

(c) inflating the balloon such that the balloon and catheter substantially occlude the blood vessel adjacent the aneurysm;

(d) delivering a sealing agent through the central lumen into the aneurysm sufficient to substantially fill the aneurysm; and (e) removing the catheter from the blood vessel.

9. The method of claim 8, further comprising the step, after the inflating step (c), of delivering an irrigation substance into the blood vessel adjacent the aneurysm through the central lumen to substantially remove blood from aneurysm sac and blood vessel adjacent the aneurysm, thereby creating a substantially clear view of the aneurysm sac.

10. The method of claim 8, further comprising the step, before the delivering step (d), of visualizing the aneurysm sac using an intravascular microangioscope.

11. The method of claim 8, further comprising the step, before the delivering step (d), of placing the aneurysm sac into a gravity dependent position.

12. The method of claim 8, wherein the catheter comprises an additional inflation balloon and wherein the method further comprises the step, before the delivering step (d), of inflating the additional balloon to block backflow from the blood vessel or from collateral blood vessels.

* * * * *